US00PP26303P3

(12) United States Plant Patent
Lee

(10) Patent No.: US PP26,303 P3
(45) Date of Patent: Jan. 12, 2016

(54) ***RHODODENDRON* PLANT NAMED 'HOMLED'**

(50) Latin Name: ***Rhododendron* hybrid**
Varietal Denomination: HOMLED

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 175 days.

(21) Appl. No.: 13/998,451

(22) Filed: Oct. 30, 2013

(65) Prior Publication Data

US 2015/0121583 P1 Apr. 30, 2015

(51) Int. Cl.
*A01H 5/02* (2006.01)

(52) U.S. Cl.
USPC ..... Plt./238

(58) Field of Classification Search
USPC ..... Plt./238
See application file for complete search history.

*Primary Examiner* — Anne Grunberg
(74) *Attorney, Agent, or Firm* — Cassandra Bright

(57) ABSTRACT

A new and distinct *Rhododendron* cultivar named 'HOMLED' is disclosed, characterized by distinctive large, single lavender flowers and a narrow, upright plant form. Plants bloom Spring, Summer and Fall. The new cultivar is a *Rhododendron*, suitable for ornamental garden purposes.

2 Drawing Sheets

Figure 1:
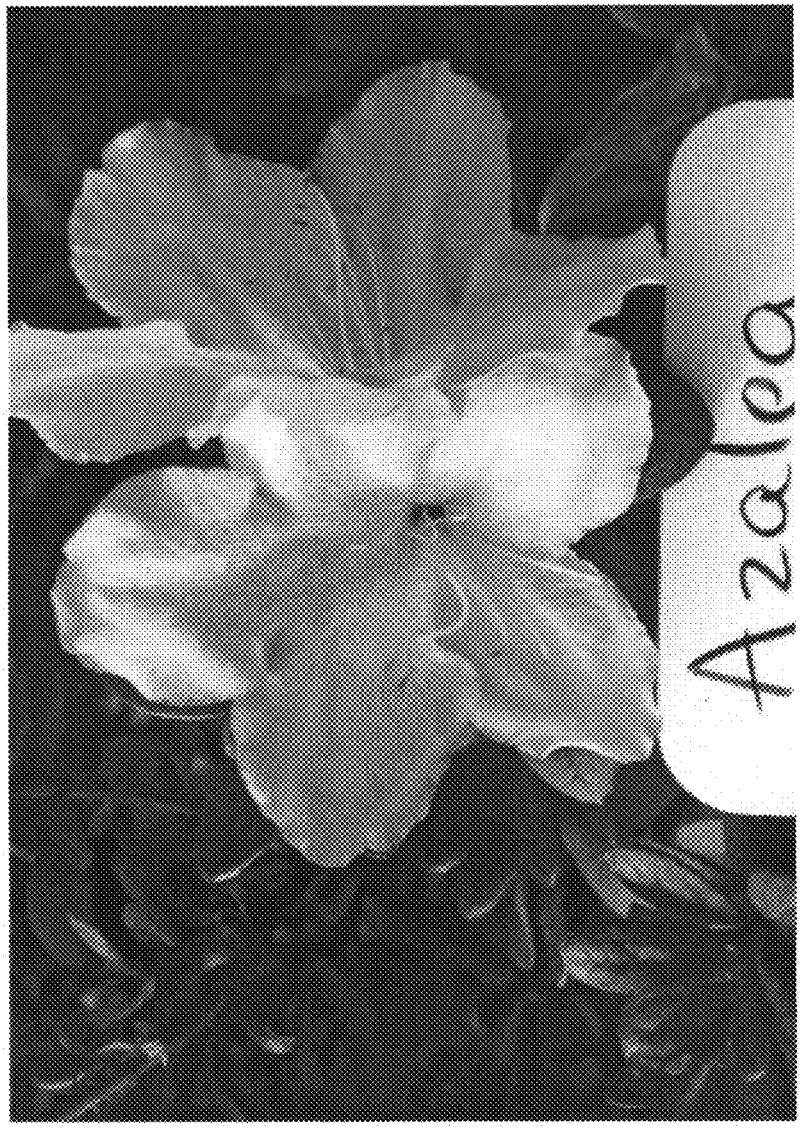

Latin name of the genus and species: *Rhododendron* hybrid.

Variety denomination: 'HOMLED'.

BACKGROUND OF THE INVENTION

The new cultivar is a product of a planned breeding program by the inventor, Robert Edward Lee. The inventor's intention was to develop compact growing *Rhododendron* hybrid plants with re-blooming characteristics. This new variety, hereinafter referred to as 'HOMLED', was discovered as a seedling, resulting from the crossing of *Rhododendron* 'Watchet', unpatented with the pollen parent *Rhododendron* 'Conleb' U.S. Plant Pat. No. 10,581. The cross was performed during the Spring of 1996, and the new variety selected by the inventor during the Fall of 2002 in Independence, La.

After identifying the new variety as a potentially interesting selection, the inventor first organized propagation of 'HOMLED' by vegetative cuttings during Fall 2002 at a commercial nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'HOMLED' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HOMLED' These characteristics in combination distinguish 'HOMLED' as a new and distinct *Rhododendron* cultivar:

1. Unique spring, summer, and fall blooming.
2. Lavender flowers.
3. Easily propagated with semi-hardwood cuttings in late spring through the summer.
4. Good specimen plant.
5. Excellent performance in containers.
6. Upright growth habit
7. Vigorous growth under normal fertilization and moisture conditions.
8. Hardy to Zone 7.
9. Attracts butterflies.
10. Large, single flowers.

COMPARISON TO PARENT VARIETY

'HOMLED' is similar in most horticultural characteristics to the seed parent variety *Rhododendron* hybrid 'Watchet'. Plants of the new cultivar 'HOMLED' however, produce lavender flowers, compared to the light pink flowers of 'Watchet'. Additionally, plant habit is overall less compact in the new variety, compared to the seed parent.

'HOMLED' is similar in most horticultural characteristics to the pollen parent *Rhododendron* hybrid 'Conleb'. Plants of the new cultivar 'HOMLED' however, produce lavender flowers, whereas 'Conleb' produces deep orange red flowers. Additionally, plant habit of 'HOMLED' is narrow and upright whereas the pollen parent has a plant shape which is more globose.

COMMERCIAL COMPARISON

'HOMLED' can be compared to the commercial variety *Rhododendron* hybrid 'Robles' U.S. Plant Pat. No. 22,762. Plants of the new cultivar 'HOMLED' are similar to plants of 'Robles' in most horticultural characteristics, however, plants of the new cultivar 'HOMLED' produce lighter colored flowers than 'Robles'. Additionally, plant form of the new variety is upright, whereas plant form of 'Robles' is spreading, with a mature size typically around 3.5 feet wide and 3 feet tall.

BRIEF DESCRIPTION OF THE PHOTOGRAPHS

The accompanying photograph in FIG. 1 illustrates in full color a close up of typical flowers of the new variety.

Figure 2:
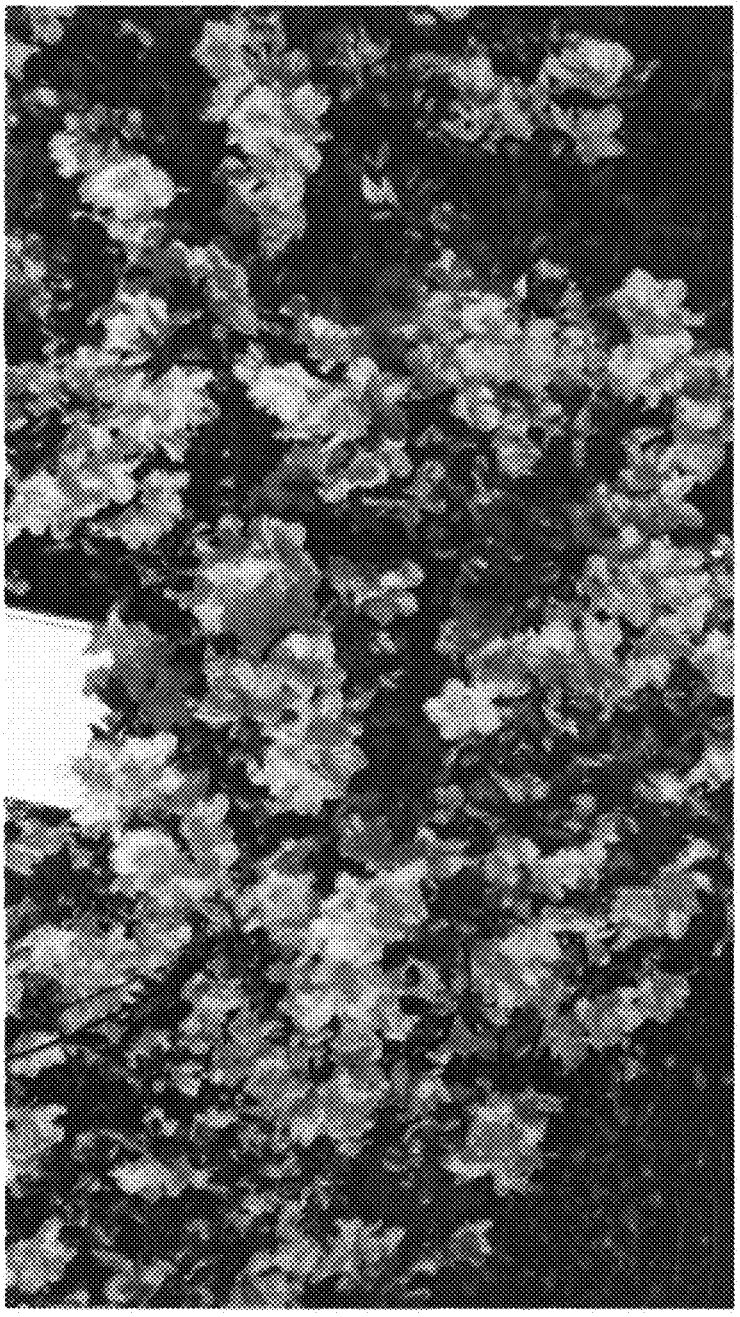

FIG. 2 illustrates a typical plant of 'HOMLED' grown outdoors in Alabama.

The plant is approximately 2 years old, and is shown planted in the ground.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HOMLED' plants grown outdoors in Loxley, Ala. Plants are approximately 3 years old, in a 3 gallon nursery container. Measurements and numerical values represent averages of typical plant types.

Botanical classification: *Rhododendron* hybrid 'HOMLED'.

PROPAGATION

Typically by semi-hardwood cuttings in Spring and Summer.

Root description: Fine, fibrous young roots, well branched. Colored near RHS Grey-Brown 199A.

PLANT

Growth habit: Narrow, upright shrub.

Height: Approximately 36 cm to top of foliar and flowering plane.

Plant spread: Approximately 45 cm.

Branching characteristics: Well branched, approximately 4 primary branches from the center of the plant. Branches occur at approximately 45° to 75° angles. Each primary branch has 4 to 8 lateral branches.

Primary branches:

- *Length of primary branches.*—Average 18 cm.
- *Diameter of primary branches.*—Approximately 0.5 cm.
- *Primary branch strength.*—Very strong, difficult to break.
- *Primary branch color.*—Near RHS Yellow-Green N144C, with age, covered with a thin bark like layer colored near Greyed-Orange 165A.
- *Primary branch texture.*—Young growth hirsute, hairs, approximately 0.15 cm long, colored near Greyed-Orange 171B. Older growth scaly, hirsute. Hairs colored near White 155D.

Lateral branches:

- *Number of lateral branches.*—Approximately 4 to 8 per primary branch.
- *Length of lateral branches.*—Average 8 cm.
- *Diameter of lateral branches.*—Average 0.4 cm.
- *Lateral branch strength.*—Very strong, flexible.
- *Lateral branch color.*—Near RHS Yellow-Green 144B.
- *Lateral branch texture.*—Hirsute.

Internode length: Average 1.0 cm.

Age of plant described: Approximately 2 years.

FOLIAGE

Leaf:

- *Type.*—Simple.
- *Arrangement.*—Alternate.
- *Average length.*—Approximately 4.1 cm.
- *Average width.*—Approximately 1.7 cm.
- *Shape of blade.*—Oblanceolate to nearly spatulate.
- *Apex.*—Rounded, blunt.
- *Base.*—Broad attenuate.
- *Attachment.*—Stalked.
- *Margin.*—Entire.
- *Texture of top surface.*—Pubescent. Hairs appressed.
- *Texture of bottom surface.*—Pubescent. More hairs present along main vein and margin.
- *Color.*—Young foliage upper side: Near RHS Green 139A. Young foliage under side: Near RHS Green 137B. Mature foliage upper side: Near RHS Green 137A, but darker. Mature foliage under side: Near RHS Green 138B.
- *Venation.*—Type: Pinnate. Venation color upper side: Near RHS Yellow-Green 144C. Venation color under side: Near RHS Yellow-Green 151B.
- *Petiole.*—Length: About 1.3 cm. Diameter: About 0.3 cm. Color: Upper Surface: Near RHS Yellow-Green 145A. Lower Surface: Near RHS Yellow-Green 151C.

FLOWER

Bloom period: Plants flower in the Spring, then begin intermittent flowering cycles in late Spring/Summer through Fall.

Flower:

- *Arrangement.*—Axillary clusters of perfect, open funnel shaped individual flowers. Typically 3 to 7 flowers per cluster.

Inflorescence:

- *Height.*—Average 12.0 cm.
- *Diameter.*—Average 13.0 cm.

Peduncle:

- *Length.*—Average 2.8 cm.
- *Diameter.*—0.3 cm.
- *Color.*—Near RHS Yellow-Green 144C.
- *Texture.*—Densely pubescent.
- *Aspect.*—Straight to very slightly curved. Angle of attachment, approximately 15° angle from stem.

Flowers:

- *Length.*—Average 4.9 cm.
- *Diameter.*—Average 5.5 cm.
- *Facing direction.*—Outwardly and upwardly facing.
- *Persistent or self-cleaning.*—Petals self-cleaning.
- *Fragrance.*—None.

Tube:

- *Tube length.*—Approximately 1.8 cm.
- *Tube width a widest point.*—Approximately 1.7 cm.
- *Tube width and narrowest point.*—Approximately 0.9 cm.

Petals:

- *Unfused petal segments.*—Length: Approximately 2.5 cm. Width: Approximately 2.6 cm.
- *Apex.*—Blunt, rounded with shallow, irregular lobes.
- *Shape of petal.*—Unfused portion, obovate.
- *Petal margin.*—Entire. Aspect undulating.

*Petal arrangement*.—Approximately ⅓ fused from base.

*Petal number*.—5.

*Petal texture*.—Smooth.

*Color*.—Upper surface at first opening: Near RHS Red-Purple N74C. Under surface at first opening: Near RHS Red-Purple N74D. Inner surface at maturity: Near RHS Red-Purple 65B, 3 upper petals dotted with Red-Purple 71D. Outer surface at maturity: Near RHS Red-Purple N74C. Upper surface at fading: Near RHS Red-Purple 73D. Under surface at fading: Near RHS Red-Purple 75D.

Bud:

*Shape*.—Elliptic.

*Length*.—2.8 cm.

*Diameter*.—1.2 cm.

*Color*.—Near RHS Red-Purple N74C.

Calyx/sepals:

*Quantity per flower*.—5 sepals.

*Shape*.—Narrow deltate.

*Length*.—0.7 cm.

*Width*.—0.3 cm.

*Apex*.—Acute.

*Base*.—Fused.

*Margin*.—Entire.

*Texture*.—Highly pubescent.

*Color*.—Inner Surface: Near RHS Green 137A. Outer Surface: Near RHS Green 137A.

REPRODUCTIVE ORGANS

Stamens:

*Number*.—10.

*Length*.—2.9 cm.

*Width*.—0.1 cm.

*Color*.—Near RHS Red-Purple 75D.

*Anthers*.—Length: Approximately 0.3 cm. Color: Near RHS Greyed-Purple 186B. Pollen: Not observed.

Pistil:

*Number*.—1.

*Length*.—4.5 cm.

*Style*.—Length: 4.2 cm. Color: Near RHS Re Red-Purple 75D d-Purple 58A. Stigma: Globular, colored near Red-Purple 75A. Ovary: Sericeous texture. Approximately 0.3 cm in diameter. Colored near Red-Purple 75D.

OTHER CHARACTERISTICS

Disease and pest resistance: Not observed to be susceptible nor resistant to normal diseases and pests of *Rhododendron* hybrid.

Temperature tolerance; USDA Zone 6.

Fruit/seed production: Not observed to date.

What is claimed is:

1. A new and distinct cultivar of *Rhododendron* plant named 'HOMLED' as herein illustrated and described.

* * * * *